US010012575B2

(12) United States Patent
Ganser

(10) Patent No.: US 10,012,575 B2
(45) Date of Patent: Jul. 3, 2018

(54) SPECIMEN HOLDER WITH ACTUATION UNIT

(71) Applicant: Zwick GmbH & Co. KG, Ulm (DE)

(72) Inventor: Franz Ganser, Laupheim (DE)

(73) Assignee: Zwick GmbH & Co. KG, Ulm (DE)

( * ) Notice: Subject to any disclaimer, the term of this patent is extended or adjusted under 35 U.S.C. 154(b) by 77 days.

(21) Appl. No.: 15/016,957

(22) Filed: Feb. 5, 2016

(65) Prior Publication Data

US 2016/0231210 A1 Aug. 11, 2016

(30) Foreign Application Priority Data

Feb. 5, 2015 (DE) .................. 10 2015 201 993

(51) Int. Cl.
*G01N 3/04* (2006.01)
*G01N 3/02* (2006.01)
*G01N 3/36* (2006.01)

(52) U.S. Cl.
CPC .............. *G01N 3/02* (2013.01); *G01N 3/36* (2013.01); *G01N 3/04* (2013.01); *G01N 2203/0411* (2013.01)

(58) Field of Classification Search
CPC .... G01N 3/04; G01N 3/02; G01N 2203/0411; G01N 3/36
USPC ............................ 73/857, 831, 833, 856, 860
See application file for complete search history.

(56) References Cited

U.S. PATENT DOCUMENTS

| 2,805,447 A | 9/1957 | Voges | |
|---|---|---|---|
| 3,375,710 A * | 4/1968 | Cavanaugh | G01N 3/04 73/806 |
| 3,908,449 A * | 9/1975 | Zuber | G01N 3/04 269/25 |
| 5,581,040 A * | 12/1996 | Lin | G01N 3/04 73/833 |
| 6,655,404 B2 * | 12/2003 | Hilaire | F15B 9/09 137/487.5 |

(Continued)

FOREIGN PATENT DOCUMENTS

| CN | 101608987 A | 12/2009 |
|---|---|---|
| DE | 1 552 653 B1 | 11/1970 |

(Continued)

OTHER PUBLICATIONS

German Office Action dated Nov. 20, 2015, in connection with corresponding German Application No. 10 2015 201 993.4 (9 pgs.).

*Primary Examiner* — Jonathan Dunlap
(74) *Attorney, Agent, or Firm* — Maier & Maier, PLLC

(57) ABSTRACT

The present invention relates to a holder having an actuation unit, particularly as a part of a material testing machine for testing specimens, for example metal test-specimens, which are held at high forces that are particularly due to the type of testing. The actuation unit operates with pressure from a pressure source. A bi-stable fluid control valve is temporarily in a first or in a second state, in particular depending on pressures at actuation sides of the valve. Besides a first actuator, which is responsible for the regular clamping force of the clamping face, to a second actuator is provided. The second actuator may also be referred to as motion unit due to its motion force to the clamping piston. The actuators arrange for a certain de-coupling of the different forces when holding and clamping specimens. Such a circuit offers the desired safety degree.

18 Claims, 4 Drawing Sheets

(56) References Cited

U.S. PATENT DOCUMENTS

| | | | | |
|---|---|---|---|---|
| 8,881,599 B2* | 11/2014 | Ganser | .............. | B23B 31/16254 |
| | | | | 73/857 |
| 9,228,334 B2* | 1/2016 | Yu | ........................... | F15B 11/08 |
| 2010/0089704 A1* | 4/2010 | Petronek | ................ | B66F 9/183 |
| | | | | 187/224 |
| 2012/0144927 A1* | 6/2012 | Ganser | .............. | B23B 31/16254 |
| | | | | 73/857 |
| 2013/0152292 A1* | 6/2013 | Yu | ........................... | E03D 1/36 |
| | | | | 4/378 |
| 2013/0152293 A1* | 6/2013 | Yu | ......................... | F15B 11/08 |
| | | | | 4/406 |

FOREIGN PATENT DOCUMENTS

| | | |
|---|---|---|
| DE | 2 158 700 A1 | 5/1973 |
| DE | 2 229 538 A1 | 10/1973 |
| DE | 28 39 341 A1 | 3/1980 |
| DE | 39 12 075 A1 | 10/1990 |
| DE | 42 28 846 A1 | 2/1993 |
| DE | 101 61 703 A1 | 7/2003 |
| DE | 11 2006 003 923 T5 | 4/2009 |
| DE | 10 2009 036 247 A1 | 2/2011 |
| DE | 11 2009 005 323 A5 | 7/2012 |
| DE | 10 2012 101 459 A1 | 8/2013 |
| EP | 2 631 496 A2 | 8/2013 |
| EP | 2 677 296 A2 | 12/2013 |

\* cited by examiner

SPECIMEN HOLDER WITH ACTUATION UNIT

SPECIMEN HOLDER WITH ACTUATION UNIT

The present invention relates to a holder having an actuation unit, particularly as part of a material testing machine for testing specimens, e.g. metal test-specimens. The actuation unit operates with a pressurized fluid from a pressure source, e.g. a pump. The holder cooperates with a fluid circuit of a material testing machine. Just as well, the invention relates to a material testing machine wherein a clamping force, e.g. for holding a test-specimen, can be applied in an especially safe manner. Such a holder can be operated according to an associated method. The method allows positioning the actuator, i.e. a closing operation and a clamping operation can be realized by means of the actuation.

TECHNICAL FIELD

As known, material testing machines, particularly for metal specimens, involve certain risks for users of the material testing machine due to their sometimes great forces (up to the range of mega Newton, e.g. 5 MN depending on the test). Test-specimens in material testing machines are often times loaded with forces in the range of kilo Newton, e.g. up to 250 kN, where there is a high inherent hazard potential already with less than the maximum load, in other words, when a material load limit is observed. One of the hazards can be traced back to the significant clamping forces that have to be so great that the test-specimen remains positioned in the test-specimen holder(s) in a safe manner during a material test. This is why the holders, or more precisely, the test-specimen holders, are so important.

The holders are available in different configurations. Centering clamping devices or center clamping devices, which facilitate aligning the specimen in direction toward a desired test axis, are particularly advantageous. Such centering clamping devices can be taken from EP 2 677 296 A2 (Applicant: Zwick GmbH & Co. KG; Priority date: 22 Jun. 2012), for example. This type of holder and similar types are then installed in material testing machines, so that a material testing machine can receive a test-specimen by corresponding holders.

The material testing machines are usually used for determining material properties, particularly for material testing of metals. A testing device is used to that end, which serves for receiving the test-specimen to be tested. The testing device can also be configured in various ways and manners. For example, so-called lever arm testing machines allow performing test measurements with tensile forces. In this case, a tensile force acts upon the test specimen, which force is translated by means of a lever arm. Details on this type of testing machine can be taken from German Patent DE 11 2009 005 323 B4 (patent holder: Messphysik Materials Testing GmbH; filing date 17 Oct. 2009). Patent document DE 11 2006 003 923 B4 (patent holder: Shimadzu Corp.; filing date: 12 Jun. 2006) describes another type of testing device. This type of material testing machine includes a column element pair and a support rod extending longitudinally to said pair. In this type, the test-specimen is attached to an attachment piece of an attachment unit, in other words, to a specific holder. In material testing machines of this structure, the transverse traverse is supported by a support rod and thus enables a material test by means of a sliding along the support rod. The patent document DE 10 2009 036 247 A1 (applicant: Zwick GmbH & Co. KG; filing date: 5 Aug. 2009) describes a material testing machine having two test-specimen receptacles, in which one test-specimen receptacle is fixedly anchored with the base frame. Said testing machine comprises two test-specimen receptacles, in particular for testing in load tests and tensile tests at springs and elastic components. In this type of testing device, a test-specimen receptacle is mounted on a displaceable actuation element. Material testing is performed in that measurement data is determined by means of a displacement transducer and a force transducer.

All of the above-mentioned and explained patent documents, in particular their explanations regarding material testing machines and their holders, shall be included in the present description of the invention in their entirety, in particular in order be able to keep the presentation on common holders and common material testing machines as short as possible, also in the description below.

As already mentioned before, clamping the test-specimen is a critical moment during a material test, in the course of which accidents may occur, for example due to insufficient attention of the operating personnel. Many accidents lead to severe injuries of the accident victims due to the forces involved in the material test.

However, not least in the technical field of material testing, clamping is important for reasons of repeatability, for reasons of reliable testing and for reasons of error reduction. For this reason, clamping mechanisms are again and again proposed in the relevant literature which either put forward prevention of accidents or the correctness of the clamping or the reliability of the clamping.

Prior Art

Due to the risk situation and in accordance with relevant machine regulations, there is the approach of operating by means of an inching operation involving a first closing movement, effecting the attachment of the test-specimen, and a subsequent clamping phase, providing significantly greater clamping forces, for example. A particularly advantageous pneumatic or hydraulic circuit, in other words a fluid circuit, can be taken from DE 1020 101 459 A1 (applicant: Zwick GmbH & Co. KG; filing date: 23 Feb. 2012), also published as EP 2 631 496 A2 (applicant: Zwick GmbH & Co. KG; priority date: 23 Feb. 2012).

Such a circuit offers the desired safety level, but it requires a certain time until the actual testing can be effected, which inter alia results from the inching operation. In particular in the case of continuous tests or when testing a greater batch of test-specimens, clamping each individual specimen is a factor that limits efficiency or through-put in such a circuit for the fluid control of the clamping jaws.

The patent document DE 39 12 075 A1 (applicant: Bundesanstalt für Materialforschung and —prüfung, filing date: 10 Apr. 1989) addresses the problem that deformation paths and testing machine elasticities are to avoided. Therefore, the test-specimen device disclosed there uses a device forming a force shunt. The force shunt device shall be able to handle a pre-clamping force bridging over the test-specimen located in the two test-specimen clamping devices of the force application means acting on another force application means. After clamping the test-specimen, the test operation starts with a yet-unloaded test-specimen, while the testing device is preloaded to a certain value.

The patent document CN 101 608 987 A1 (applicant: Taiyuan Heavy Machinery Joint; priority date: 24 Jul. 2009) describes another type of a material specimen testing device.

The hydraulic switch device shown in CN 101 608 987 A1 is said to clamp a clamping device having a piston, which clamping device is able to clamp an expansible tube. The position of the pistons is measured by means of distance sensors located in the pistons. Depending on the measurement signals, a relief valve can be operated. In case of an overload in the hydraulic switch during a pressure test on the tube, a relief valve can be opened. This serves for providing protection to the switch. In other words, CN 101 608 987 A1 explains the topic of avoiding pressure peaks in reactions produced by the test-specimen in the hydraulic switch disclosed therein.

German patent DE 28 39 341 C3 (patent holder: Daimler Benz AG, date of disclosure:

13 Mar. 1980) relates to switches having pneumatic flip-flops, wherein a flip-flop is to operate in a "high-pressure range" up to 8 bar. A flip-flop always is to be in a stable state, regardless whether a signal is applied to its signal input or not. As a field of application, reference is made to clamping devices, e.g. for tools being clamped by means of an operating piston. Although it is generally known that clamping of tools for the machining of materials needs to meet different requirements than in material testing, however one exemplary embodiment refers to an operation by means of a two-hands control for pneumatic clamping devices, which control is to prevent that a hand may erroneously get between the advancing operating piston and the workpiece to be clamped. The pneumatic switch according to FIG. 1 of DE 28 39 341 C3 operates with four 5/2 valves, which are actuated by means of control pressure. As a safety measurement, it is proposed that by the design and configuration of the control, control personnel should be forced to keep both hands on the pulse generator due to a control switch until the workpiece is clamped, otherwise the valve is reset. In a more abstract manner, in the back part of the patent document it is noted that effectively it is to be operated with binary counters as a result. That means, a complicated switch is to be realized pneumatically due to the high number of counting members.

The patent document DE 42 28 846 C2 (patent holder: Güllmeier; filing date: 29 Aug. 1992) describes a pneumatically-operated, pressure-translating operating piston for a fast mode and a force stroke, which can also be used for clamping workpieces. For the fast mode, the operating piston is applied with the normal operating pressure over its entire surface via a first connection. The force stroke is to be generated by the plunging of a displacing piston in to the pressurized air already pre-loaded for the fast mode. The valve control used therefor is quite simple, though. Two valves are provided, the first valve serving for the fast mode and the return stroke, while a second valve may add the force stroke after the effected fast stroke.

Such a switch might not meet general, normed standard requirements.

A safety device according to DE 2 158 700 A (applicant: Festo-Maschinenfabrik Gottlieb Stoll; filing date: 26 Nov. 1971) is to serve for controlling the pressure medium flow to a consumption point, such as a press, a punch or a bending device. By a similar operation of two manual valves, a pressure fluid passage can be released from a main valve to a consumption point. To that end, a "AND" member, which is to be configured as a double- pressure-valve (German: Zweidruckventil) is connected in parallel to an "OR" member, which is to be configured as a double control valve (German: Doppelsteuerventil). This is used for actuating the main control valve for supplying the consumption point. In FIG. 1, a so-called consumption valve is connected upstream the consumption point, which consumption valve is indicated in a cylindrical shape and having a spring on a side of a piston facing away from the main control valve. At least with regard to a presence of a pressure source, FIG. 1 seems incomplete. It is mentioned as a reason for obtaining an increased safety for the arrangement of consumer valve, main valve and consumption point, that the safety device could be operated under a lower pressure. That means that this is mainly about the reduction of the pressure in the switch; however, in contrast, the clamping pressures involve particularly high pressures.

A pneumatic or hydraulic clamping device for workpieces having a movable or fixed clamping part is described in DE 1 552 653 C (patent holder: J. Gottlieb Peiseler company; filing date: 9 Feb. 1966), in which the movable clamping part is driven by a cylinder-piston drive and a manually-operable control body is provided between a cylinder and a pressure medium source. A force considered to be not dangerous of up to 15 kp (approximately 150 Newton) is mentioned in the document. The safety function is realized essentially by means of a tappet and a carrier in the form of a set screw, which set screw is to be set to a thickness of a workpiece. The set screw not only serves for actuating the tappet but also as a stop for limiting a movement in conjunction with a counter stop. The sequence of movement upon clamping is to be such that the tappet first releases the entire pressure or final pressure, respectively, of the pressure source and the adjusting screw limits a path on the counter stop surface which is travelled-through under said high pressure. The high pressure can e.g. be caused by a weight force in the range of 250 kp. A hazard, e.g. in the form of a finger injury is said to be reduced according to DE 1 552 653 C due to the small, limited distance.

The U.S. Pat. No. 2,805,447A (patent holder: Voges; filing date: 5 Nov. 1953) describes an arrangement for an injection molding machine. An extension movement is to be carried out at a low pressure. High pressure is to be applied at the end of the extension, wherein (simply undetermined technical) means are to be provided, by means of which the extension shall be allowed to be interrupted prior to the application with the high pressure. For applying a (supposed) low pressure of approximately 1700 PSI (approximately 117 bar) a double piston arrangement is provided, wherein the low pressure around a pressure rod piston (ram) accounts for the biggest extension path. The piston is moved to the high-pressure position by means of the low pressure. Here, it is provided that a switch arm activates a switch, wherein a valve in a bypass line is closed, so that the entire pressure of the pump is applied to the piston. As a safety measure, it is to be possible to interrupt the extension if a hand or an arm was brought between the molding parts by incidence.

Various disclosures of the applicant Mayer, Max from Burlafingen concerning a main patent with the official document number DE 22 29 538.1 relate to configurations of pneumatic clamping devices, in each of which a small shear force and an increased clamping force shall be applied at the end of a lead run by means of in each case one cylinder, if a hard object, e.g. made of metal, is detected. Merely by way of example, DE 22 29 538.1 provides a sensor pin, which sensor pin switches a venting system on a rear side of a main piston and therefore simultaneously the contact of the pneumatic clamping pressure, such that a pressure continuously applied to the main piston can be effective. It is described in an exemplary embodiment thereof in a deviating manner, that the shear force for a closing movement is to be achieved in that a pressure medium streamed onto the rear side of the piston is guided to the front side, wherein a resistance of a pressure spring must be overcome. The sensor, in a state after running to a hard material, effects the blocking of the air way between the main cylinder chambers and a venting of the front cylinder chamber.

The patent document DE 101 61 703 B4 (patent holder: FESTO AG & Co. KG; filing date: 15 Feb. 2001) refers to a venting device for controlled venting of a pneumatic drive. Worded in general, a movement of a drive piston having two working chambers for the operation of random components or devices can be taken therefrom. A change valve is interposed between the two working chambers, which valve controls the exhaust of air from the two working chambers. In this case, the change valve shall only close the inlet, the assigned working chamber of which is subjected to the temporarily highest pressure drop. By means of the continuous venting of both working chambers, the pressures prevailing therein are to always exert equally-high pressure forces onto the drive piston in order that said piston remains at standstill. By means of this, e.g. in case of an emergency-off function, an undesired further movement of a pneumatic drive is to be prevented to prevent damages to humans or to the machine.

It is remarkable that many of the presented switches or devices have been designed for tooling machines. The particular conditions for material testing machines, which at least partially arise from standard specifications, often times can not be fulfilled by the mentioned switch circuits and components.

Some of the documents cited in the foregoing explain the principle of operating with two different pressures, therefore proposing suitable components and assemblies, which are said to be included in their entirety in the extent of disclosure of the present description of the invention. Further, the details concerning the individual safety designs are said to be part of the present disclosure.

Object of the Invention

Ideally, a circuit should provide a most high safety level on the one hand, and be suitable for a routine test, particularly as a part of the material testing machine, on the other hand. That means that aspects like the reduction of measuring errors, set-up times and reproduction deviations and variations should be considered and handled by a corresponding holder, its material testing machine and its operation. However, the common piece of wisdom lies with the fact that high velocities may produce a significant risk during a material test (see the phrase "speed kills"). The question is: Which actuation means is a material testing machine, more precisely its holder, to be equipped with, where the material testing machine poses only a slight chance of an accident risk by means of squeezing of body parts prior to the actual material test.

Description of the Invention

The object of the invention is achieved by means of a holder or an actuation unit, a corresponding material testing machine and a suitable system.

A holder, which may commonly also be referred to as specimen holder, in a material testing machine is used for holding a test-specimen to be clamped, particularly for providing said specimen reliably at one location against a test force. When performing the test, the specimen shall not be capable of being released from the holder. Often times, holders are additionally used for applying the test force to the specimen. The forces are so significant or great that the holder receives its holding or clamping force for the sample advantageously in a pneumatic, hydraulic or electrical manner, e.g. by use of linear motors. This is why a material testing machine includes an actuation unit, by means of which the jaws, e.g. the retainer jaws, can be shifted and/or displaced. Combinations of the different types of motion and means are also possible, e.g. electro-pneumatic, or e.g. electro-hydraulic. That means the holder can be installed in a material testing machine for specimens. Actuation of a moveable part such as a clamping jaw in the holder is possible by way of an actuator. A fluid, such as pressurized air or a hydraulic medium, e.g. a hydraulic oil, receives its pressure from a pressure source. The material testing machine or the holder, respectively, include a port for a pressure source or even include the pressure source per se. That means, at least a first actuator is provided in the holder, which may be loaded with a fluid from a pressure source.

Depending on the test-specimen, e.g. depending on the length and/or size of the contact and/or holding regions, it is required to use a clamping device having one or multiple small clamping jaws, a clamping device having one or multiple medium clamping jaws, or a clamping device having at least one large clamping jaw. Small clamping faces are in the range of 30 mm×30 mm. Large clamping jaws have holding surfaces of greater than 100 mm×100 mm. Ideally, the holding surface becomes a clamping surface particularly when applied with a greater force (compared to the force during the holding phase).

In one configuration, the actuation unit may be realized as pneumatic or as hydraulic circuit having corresponding valves. A bi-stable fluid control valve is provided as a possible valve between the pressure source and the actuator. A fluid control valve should comprise at least a first and a second state. Additional states may be provided in the fluid control valve. In the simplest configuration of the circuit further described below, a component such as a bi-stable fluid control valve is required, which provides at least two states. In more complex embodiments, a multi-state fluid control valve can be installed in place of the two-state fluid control valve. A counting member, by means of which various states may be set, operates in a similar fashion.

The actuator includes at least one clamping piston. The clamping piston may be set to a certain position by the interplay between the fluid control valve and the actuator.

Besides the actuator, responsible for the regular clamping force of the clamping face, a second actuator is provided. The second actuator may also be referred to as motion unit due to its motion force to the clamping piston. In other words, an actuation force is applied to the second actuator. For applying the actuation force, the second actuator is connected to the clamping piston, e.g. directly and immediate, alternatively also indirectly. The actuation force provided by the second actuator prevails at the clamping piston, for example, via a mechanical connection or via a fluid force transmission means. The second actuator enables overcoming at least a friction force of the clamping piston by means of the actuation force. Advantageously, the actuation force is at least greater than a friction force of the clamping piston. The clamping piston of the holder is moveable by the actuation force, particularly unidirectional, on an actuation path. By means of the actuation force, the clamping piston takes a closing position in the absence of additional pressures (wherein of course the atmospheric pressure may be neglected in the first instance). When taking the closing position, said closing position can be determined by means of the available actuation path. The actuation path of the clamping piston may be limited by an actual obstacle, such as a stop, particularly on a test-specimen.

The additional actuator, i.e. in particular the second actuator or the additionally acting actuator, respectively, exerts an actuation force, which shall be directed predominantly into one direction, particularly for reasons of efficiency. By means of the actuation of the actuation force, a closing pressure may be applied to the piston. The clamping force, respective the pressure that the clamping force can be traced back to, is also directional. Ideally, the clamping force and the actuation force act into the same direction. However, clamping force and actuation force are to be of different size so that they can be used for assuming different tasks. The clamping force and the actuation force act on a specimen to be inserted once the closing position has been taken. In a favorable configuration, the clamping force and the actuation force are rectified at the piston. Ideally, clamping force and actuation force are superimposed to one another. In other words, the second actuator acts into the same direction as the medium generating the pressure to the piston (means for the clamping pressure or for the clamping force).

The bi-stable fluid control valve takes a first state or a second state. At least one first valve control line is present in the circuit. The fluid control valve is connected to the first valve control line. A fluid pressure in the first valve control line has an influence on the state of the fluid control valve. A second valve control line, which is also connected to the fluid control valve, provides the fluid control valve with a second control pressure. The second control pressure can also have an influence on the state of the fluid control valve. The first valve control line is connected to a chamber of the actuator. The chamber pressure of the actuator prevails at the fluid control valve via the first valve control line. With the fluid control valve being supplied with pressure from the actuator, a comparison of the pressure to a preset threshold pressure at the fluid control valve is possible. The value of the threshold pressure is a pressure value, by means of which it is determined whether a state change from the first state into the second state is performed or not. If the pressure in the first valve control line is below the threshold pressure, the instable fluid control valve may change into the second state. In the fluid control valve, the threshold value may be set, for example, as a pressure in a pressure range of 0.8 to 1.1 bar, such as 1 bar (in the case of a pneumatically operating valve), for comparison with a supplied actuation pressure. A higher set threshold pressure may also be advantageous, e.g. depending on the operating pressure range of a material testing machine. In one embodiment, the threshold pressure may be set at for example 1 bar above the minimum operating pressure of the operating pressure range as a reference. A higher threshold pressure than 1 bar can be useful in a hydraulically operating actuation unit, for example, i.e. in a hydraulic fluid control valve.

However, a state change of the fluid control valve ideally also depends on a switch signal. The switch signal should be present at the fluid control valve. The switch signal can be transmitted to the fluid control valve via the second valve control line. In other words, the second state can only be taken if the switching is signaled or permitted by both the first valve control line and the second valve control line. Falling below the threshold value may be referred to as a first switch signal. Accordingly, a switch signal in the second valve control line may be referred to as second switch signal.

It is to be mentioned at this point that the sequence of the switch signals has not been addressed yet.

In one embodiment, the second switch signal may be present at a time prior to the first signal. However, the change into the second state occurs only when the pressure from the chamber of the actuator allows the pressure in the first valve control line to fall below the threshold pressure. By comparing the pressure to the threshold pressure, a safety check is automatically effected, which prevents an arbitrary change into the second state, possibly in a risky situation. The requirement of a switch signal, particularly of a second switch signal, in the second valve control line enables binding the second state to a switch precondition, particularly further increasing safety. Said switch precondition is to be generated preferably by operating personnel. This way, the changeover into the second state of the fluid control valve, which might involve an increased risk potential, can be safeguarded at least twice. It is even possible to bind the provision of the switch signal to the fulfilling of a multitude of safety conditions as a first condition to be fulfilled, e.g. the actuation of push-buttons, e.g. the observance of light barriers.

Just as well, it is possible and conceivable that the second switch signal prevails only when the first switch signal had been generated in advance; i.e. reverse to the above described sequence.

It may also be said that the fluid control valve only changes into the second state when a pressure falls below a threshold pressure in a first valve control line, which can be supplied with pressure from a chamber of the actuator, i.e. supplied under regular circumstances, and when additionally a switch signal prevails in the second valve control line at the fluid control valve. If the pressure in the first valve control line is greater than the threshold pressure, the second state can not be taken.

Thus, the safety concept of the holder includes an intrinsic part and a part configured for an extrinsic influence of the actuation unit, so that an erroneous operation may be excluded to a large extent. In this point of view, the second switch signal may be considered as an extrinsic condition. In one embodiment, the first condition, i.e. the intrinsic part, depends on pressure conditions or ratios in the circuit, in particular at one or several locations of the circuit system.

The material testing machine, particularly for testing metal test-specimens, comprises a holder for test-specimens. A pressurized fluid can be supplied to said holder. The fluid may provide the holder with a clamping force for a clamping state. For example, the holder may comprise a first and a second clamping device, by means of which test-specimen end regions can be clamped. Material testing machines expose test-specimens to at least one controlled load, in some cases a repeated load, such as a clamping force. Tensile- and/or pressure testing machines are examples of material testing machines requiring a particularly safe hold for a test-specimen, particularly due to specimen loads up to destruction or rapture. In the case of material testing machines which are used such that frequent specimen changes are to be effected, i.e. the specimen changes may be considered as part of a routine work, the risk of non-attention during the specimen change increases.

Usually, the holder is intended for a force-fit operation. The clamping jaws are to hold the test- specimen in a force-fit manner. Clamping, respectively holding the sample is effected by means of the clamping jaws in a force-fit manner. If a finger is located between the clamping jaws, the latter can oftentimes not be pulled out from between the clamping jaws due to the clamping pressures.

A hazard or risk, invoked by categories of operating errors, is at least significantly reduced—if not even completely excluded - when equipping the material testing machine accordingly. The holder comprises a position that can be referred to as open position. In the open position, e.g. the test-specimen can be removed from the holder. The holder comprises a position that can be referred to as a closing position. If the holder is in the closing position, a clamping state can be taken. The closing position of the holder may be different from a clamping position of the holder. The closing position and the final clamping position may be the same position, but do not have to be the same position. The open position and the closing position of the holder may also be referred to as positions free of clamping forces. A movement of the holder, in particular of the clamping device, relative to a test-specimen can be performed by a motion unit. The motion unit is connected to the holder. Preferably, the motion unit is in a permanently active operating state, i.e. the motion unit is operated in an uninterrupted manner, that means even if no movement is effected. The motion unit serves for taking a preferred position of the holder. The closing position may be such a preferred position. In such a preferential position, at least a first hold-open force prevails at the test-specimen. In one exemplary embodiment, in a holder having two clamping devices or when using two holders, the first hold-open force may be provided by a second actuator, and a second hold-open force may be provided by a fourth actuator. In other words, an actuator is capable of generating the motion of a motion unit. The provision of a motion drive by means of a safety force vector is possible. The safety force vector provides the force for a drive of a clamping jaw. A safety force vector is to be understood as a directional force, the magnitude of which preferably does not exceed 150 Newton (N). A safety force vector or a closing pressure, respectively a first clamping pressure, can be limited by way of a predetermined spring rate or a pressure relief valve, for example. A closing pressure of 2 N/mm$^2$ can also be considered as safe, if with respect to a risk of injury, body injuries are to be prevented. Because of the provision of a limitation, safety is provided by both a safety force vector and a closing pressure, i.e. also when using a first and a second, e.g. smaller than the first, clamping jaw size. A preferred direction leads from the open position towards the closed position. It is also possible to have a safety force vector, e.g. from a spring, cooperating with a closing pressure, e.g. from a safety fluid pressure cylinder unit. A (predetermined) threshold value of a clamping pressure or a closing pressure, respectively, can preferably only be surpassed in the closing position by means of the actuation unit.

A method for actuation, which offers a special protection during the handling, may for example be used with holders for test-specimens or tools (of the material test). The method can be realized in a particularly advantageous manner together with an above-described actuation unit. The method makes use of or is based on the fact that at least one actuator and at least one bi-stable fluid control valve, also referred to as valve only, are present. At least one, preferably two connecting pressure medium lines are located between actuator and valve. One pressure medium line also leads at least from the fluid control valve to a pressure source of a fluid. At least in one switch state, the fluid control valve is capable of providing a connection to the pressure source. The actuator is capable of taking at least one position, which is no longer the initial position. One of the actuator positions, e.g. the first position, is a closing position. A second position may be provided as a hold-open position or open position. Instead of a second position, there may also be a movement play (range). Outside the closing position of the actuator, the receiving region opens up, particularly for inserting a test-specimen or a tool into a holder.

The actuator is kept open by means of a hold-open pressure. The hold-open pressure may be a pressure in the actuator per se. A safety closing force is applied by the actuator, which is opposed to the hold-open pressure. The safety closing force can be provided in the interior of the actuator. In another configuration, the safety closing pressure or part of the safety closing pressure may be provided from outside the actuator. The hold-open position is abandoned when the hold-open pressure is too low to compensate the safety closing force. The hold-open pressure acts upon the fluid control valve and determines a switch state of the valve, in particular a pressure-free state, like a pressure source blocker for the actuator. A change of the switch state enables building-up a clamping pressure in the actuator. The clamping pressure acts in the actuator in a direction that is opposed to a direction of the hold-open pressure. The build-up of the clamping pressure is effected from the pressure source through the fluid control valve in the actuator, once a sufficient decrease of the hold-open pressure has taken place. In particular, the hold-open pressure should have decreased so much that the safety closing force has an effect on the motion of the actuator. The hold-open pressure is typically subject to a pressure-time-characteristic curve. The hold-open pressure correlates with a motion of the actuator into the closing position. The hold-open pressure in the closing position may also be referred to as closing position pressure of the actuator. The closing position pressure is a threshold pressure that can be stepped under by the fluid pressure, which can be lead out of the actuator via at least one pressure line. Once the hold-open pressure is reduced, a state change of the fluid control valve is possible. In other words, the hold-open pressure protects the fluid control valve against a state change in a through-state for pressure from the pressure source. The through-state can be taken upon request or if it is requested in the following, i.e. after the decrease of the hold-open pressure. An input unit is provided to that end. The input unit may be assigned to the actuation unit; in this case the input unit is part of the actuation unit. The input unit outputs the request for a state change to the fluid control valve. In other words, the fluid control valve switches into a through-state, if at least two, preferably three switch conditions are fulfilled. As a result, the built-up of a clamping pressure is at least twice protected against an untimely pressure build-up.

By means of a strict force limitation in motion phases of the holder, in particular when performing processing steps prior to the actual clamping, and by means of the coupling of the activation of the clamping force of the holder upon presence of intrinsic pressure differences, particularly below a threshold value, the accident risk resulting from potential erroneous handling is significantly reduced in particular when working with material testing machines.

Advantageous embodiments and further developments will be described in the following, which can disclose an inventive aspect per se or in a combination thereof.

Depending on the type of material testing machine or the holder installed in it, one or multiple clamping jaws are provided. One such clamping jaw should be able to take multiple, at least two final positions. One of the positions should be a closing position. As a consequence, a holder is to be configured such that at least one clamping jaw of the holder is capable of taking a closing position. The taking of the closing position is ideally not caused by the first actuator, which is responsible for the clamping force, but by a second actuator of the clamping jaw. It is advantageous if said second actuator, wherein one individual second actuator is provided per main actuator, comprises an actuation force limitation unit. In other words, the force by means of which the closing position is taken, should be limited to an acceptable value. An actuation force may be provided by means of the actuation force limitation unit. In that case that the actuation force prevails over a longer time period, i.e. if an actuation force is continuously provided—during a certain phase—, the actuation force results in the clamping jaw taking a closing position. Stops and other obstacles, which can prevent the taking of the closing position, are not considered. However, the closing force is limited upward. The closing force remains in a low region. A low region of a force is below a force corresponding to a weight of 10 Kg to 15 Kg. Additionally, or in an alternative embodiment of the limitation, a permanent pressure below the maximum pressure, exerted by the clamping jaw, can be controlled.

Advantageously, the actuator can be realized as a linear cylinder. A linear cylinder as actuator offers a reliable translation from pressure to travel and vice versa. For moving the actuator, the actuator may be applied with source from a pressure. Suitable means for the provision of a source pressure are pumps, pressure reservoirs or ports to high-pressure lines.

The actuator may take different positions. One position may be referred to as a pressure built-up position. The actuator preferably also has two chambers, of which one chamber is a hold-open chamber. Pressure in the hold-open chamber ensures one position of one clamping jaw, in which the sample to be arranged in front of the clamping jaw is not held, particularly in the case that the force from the pressure in the hold-open chamber exceeds the force form an opposed pressure, e.g. exerted in a closing chamber. A pressure build-up position of the fluid control valve is opposed by a fluid flow-off pressure of a hold-open chamber of the actuator, in particular the linear cylinder. Said pressure prevails at the fluid control valve at the control side through the first valve control line. The flow-off of fluid is supported by a pressure in one aspect. The fluid control valve comprises one or multiple control sides. Other ports include operating or pressure ports. By means of a state-determining valve such as the fluid control valve, the position of the actuator can be determined, e.g. for taking the closing position.

In a material testing machine, in particular in such machines in which a sample is to be clamped at two locations, preferably two holders are provided. Each holder should have at least one (main) actuator. In this case, at least two actuators are provided, which are used for clamping the sample. In a material testing machine configured for a manual sample exchange, the actuators used for clamping are preferably independent from one another, in other words, each is configured to be actuated with one input unit. In a material testing machine, respectively in two holders present in a material testing machine, a first actuator and a third actuator are configured to be actuated sequentially via an input unit. It is also possible, e.g. in an actuation unit, to actuate a first actuator via a first and a third actuator via a second, particularly in each case bi-stable fluid control valve with in each case one assigned input unit. Actuation of the actuators used for a two-sided clamping of a sample can be effected with a favorable time offset, e.g. at least two seconds, in a time-efficient and safe manner. In such a configuration, the first actuator is clamped first, and after that, in other words sequentially, the third actuator is clamped. In such a configuration, the clamping process caused by an actuator may be given undivided attention by an operator. In an alternative configuration, the actuators may operate in a synchronous manner in a material testing machine, which e.g. cooperates with an automatic sample feeder, or also in a material testing machine which includes an automatic sample positioning device.

In particular, the actuators of an actuator pair may be coordinated to one another in terms of their movements. The term "synchronized" in a particularly favorable configuration can be understood to that effect that the motion of one actuator can be found also as a motion of the other actuator in an (at least) proportional relationship, in particular during the same phase. In another configuration, a motion can also be present as a synchronized motion in that a settable time interval, e.g. a millisecond interval, is preset between the beginning or the end of a first motion of one actuator and the beginning of a second motion of the other actuator. By means of such a synchronized motion sequence, e.g. a relaxation of the test-specimen is allowed after a first clamping. The motion of the first actuator corresponds to the rectified motion of the second actuator. In this case, at least one switch valve is connected downstream the actuators at the side of the fluid flow-off. Said switch valve is preferably a two-position check valve, which can be switched by means of pressure differences. An actuation pressure prevails at the fluid control valve. Said pressure is provided by the greatest fluid flow-off pressure of the actuators through the switch valve. In the case that two holders are provided, particularly operating in a synchronized manner, the actuators of one holder may be referred to as first and second actuator and the actuators of the other holder may be referred to as third and fourth actuator.

As a result of the presence of a two-position check valve in the circuit, the valve creates a circuit, in which the risk potential that may be caused by each holder of the at least two present holders can always be concentrated to the holder, in the hold-open chamber of which the in each case greater pressure prevails at a certain point of time. The presence of a pressure in a hold-open chamber indicates that a termination of a hold-open state has not been finished in at least one holder. As a result, there may be an interspace in the region of the one holder, respectively on the one holder, in particular in the region of or in front of the holder having the higher pressure in the hold-open chamber compared to the pressure in the other holder, in which interspace possibly a finger is present. The supply of the clamping force to both actuators is effected simultaneously. Only upon termination or abandonment of the hold-open state, in other words, when the open position of both holders is closed, both of the first and the second holder, a force increase beyond the force from the safety force limit is possible.

Special thoughts have also been made in terms of the design of the pressure conditions. The clamping cylinder, which is preferably guided in a linear cylinder, comprises a hold-open face and an actuation face. The hold-open face and the actuation face are separated from one another by an impermeable region. Advantageously, the clamping piston is used as an impermeable region, so that particularly the clamping piston presents a fluid limit. The hold-open face can be applied with a (first) fluid pressure. The actuation face can be applied with a (second) fluid pressure. In one configuration, the fluid pressure acting on the hold-open face is greater than the fluid pressure acting on the actuation face. Keeping the hold-open position can be facilitated in that the clamping piston is provided with a fluid pressure relief of the actuation face. By means of a fluid flow-off, the fluid located in front of the actuation face may discharge from the actuator. Preferably, the fluid flows off via the fluid control valve. By means of the applied fluid pressure at the hold-open face, the clamping piston is secured in the hold-open position. A motion of the clamping piston is possible only after stopping a fluid pressure application, in particular within the meaning of a pressure below a minimum pressure, at the hold-open face. The hold-open face subject to fluid pressure can be relieved from pressure by the flow-off of fluid away from the hold-open face via a predetermined flow resistance, particularly formed by a line cross-section and a line length. A motion of the piston and thus of the hold-open face arranged on the piston and of the actuation face arranged on the piston from the hold-open position is effected in a pressure-limited flow-off mode. The hold-open position of the clamping piston is determined by way of a position of the piston. It is possible to configure the circuit to that effect that driving toward the hold-open position is provided below a limited summary safety force, particularly in the size of a closing force.

In a holder known from many configurations of the prior art, the clamping piston would present a risk of injury. In the holder according to the invention, the risk of injury is reduced because of various measures. Some measures haven been addressed before. Further measures will be explained in the following.

As a further measure it may be provided that at least at one side, particularly at the actuation face side, at least one of a spring and a fluid pressure cylinder unit are assigned to the clamping piston. At least one of the spring and the fluid pressure cylinder act as an actuator, in particular as a second actuator. The force, particularly the closing force, which can be exerted by at least one of a spring and a fluid pressure cylinder, is limited. By means of the limitation, the clamping piston may be moveable with at least one of a closing force of maximum 150 Newton and a closing pressure of up to maximum 2 N/mm$^2$. It has turned out that force below 150 Newton, with larger clamping jaws, such as clamping jaws having an area of 81 cm$^2$, pressures of less than 2 N/mm$^2$ to 3 N/mm$^2$, such as approximately 2.5 N/mm$^2$, usually do only cause an unpleasant pressure, but no injuries. Depending on the actual clamping face, the threshold value among the two threshold values of force (150 Newton) and pressure (2.5 N/mm$^2$) takes effected which is the lowest among the said values, provided that force is calculated into pressure and vice versa. The lower threshold value of the two available threshold values determines the force and the pressure exerted by the clamping face of the clamping jaw.

The sequence control resulting from the circuit predetermines certain operating steps. One operating step requires that additionally a safety device is actuated before being able launching the clamping process. For example, both hands of an operator may have to touch push-buttons before one holder or (first) actuator, preferably both holders likewise, are capable of clamping.

An actuation unit having an input unit is particularly advantageous. The input unit enables the actuation unit to perform control commands. For example, the control commands may be generated by a manual actuation of a sensor, preferably a sensor pair spaced apart from another by a certain minimum distance, such as a temperature sensor. A hold-to-run safety control is suitable as an input unit. Preferably, two hold-to-run safety controls are provided, which have to be actuated with both hands due to a distance of more than 30 cm between said hold-to-run safety controls. Hold-to-run safety controls may operate with a fluid or electronically. An additional actuation unit may be a light barrier system. The control signal can be represented as a pressure change or voltage change in a line, such as a pressure line or an electric line, if particularly two hold-to-run safety controls are actuated both at the same time. In one actuation state of the input unit - in one embodiment—the input unit fulfills all requirements that need to be present for generating a control command. The control signal may be added to the fluid limitation signal. Preferably, the control signal prevails in a secondary manner at the control side at the fluid control valve. The control signal may also be referred to as actuation control signal. An actuation control signal is a request for a state change of the fluid control valve. A position change of the fluid control valve is called up. However, the position change is only effected if at the control side, in other words at the primary control side, a pressure prevails at the fluid control valve that is below a threshold pressure. This way it is prevented that the fluid control valve gets into a second position by an arbitrary, one-handed actuation of the input unit, in which position a clamping pressure is increased to exceed a threshold value. The phrase "at the secondary control side" means that an admission of actuation of the fluid control valve is hierarchically below the primary, in particularly intrinsic, control of the fluid control valve.

The actuation unit comprises at least one, preferably two, a first and a second, motion valve. The motion valve comprises at least a first and a second flow-through control. Preferably, the motion valve is actuated by a component of the actuation unit such as the input unit, particularly a second input unit. At least one of the motion valves may be configured to be electronically actuated and change the through position in the type of a switch due to a control signal. The first flow-through position of the motion valve connects a pressure source to the first control line. Preferably in one of the positions, the fluid gets into the hold-open chamber from the pressure source. The actuator is opened by pressure supply. In the second flow-through position, fluid flows-off from the first control line into a fluid reservoir. The fluid reservoir may be a sump or a storage container. In the second flow-through position, fluid may also get from the hold-open chamber in direction of the fluid control valve, in particular via a control branching of a connecting line for pressurized medium into the first control line. The fluid flow-off from the hold-open chamber at least interferes with the fluid flow-off from the first control line. A back pressure opposes a flow-off of fluid from the first control line in direction of the fluid reservoir. The fluid is being forced back in the first control line. In other words, fluid may also penetrate into the first control line from the hold-open chamber when flowing-off and thus build-up a counter pressure in the first control line. Preferably, a flow-off cross-section of a line from the hold-open chamber and the first control line is greater than or equal to a through cross-section of the motion valve in the second flow-through position. It is also possible installing an additional throttle valve, which prevents a backflow into the fluid reservoir in an unidirectional manner. By means of at least one of a throttle valve, such as a size-adjustable flow-off opening or bore-hole, and a ration of the two flow-off cross-sections, a time constant can be preset for the flow-off of fluid from the hold-open chamber. The time constant scales with a predetermined hold-open chamber volume change, wherein in particular an actuation force causing the volume change prevails in a limited, preferably essentially constant, manner. The time constant is particularly greater than the human reaction time and may be one second or more, for example. In the first flow-through position, a flow resistance is as low as possible, so that the hold-open chamber can rapidly be filled through the motion valve and the holder can be opened.

The motion valve may be switched back and forth between at least two positions. By means of the motion valve, the actuator is brought into different positions. The pressure source may be a pressure source that generates pressure in a manner not controlled within a pressure range. A reliable pressure regulation to one single value to be kept is not necessary. The pulsed pressures often times generated by uncontrolled pumps may be directly fed to the motion valve.

One functionally favorable embodiment of the motion valve comprises at least one switch state, preferably at least two switch states, such as e.g. a first and a second switch state. At least the second switch state is preferably a bi-functional state. According to a first aspect, a pressure drop at the actuation side of the fluid control valve is enabled in a particularly hydraulic or pneumatic actuation unit in the second switch state. A pressure has reached below a threshold pressure when a pressure value prevails at the fluid control valve which is lower than a predetermined pressure. The second switch state includes a through connection between the actuation side and one, particularly pressure-free, storage container or another reservoir. According to a second aspect, the pressure source used for supplying the hydraulic or pneumatic system may be blocked, so that a fluid flow connection from the pressure source to the actuation side of the fluid control valve is blocked. The through-flow block is unidirectional and is located particularly between the pressure source and a branch. Here, fluid may not get from the pressure source into the first valve control line. The branch connects the fluid control valve on the one side, namely at the actuation side, and on the other side the actuator, preferably the hold-open chamber, to the motion valve. It may also be said that the motion valve, in particular the second switch state of the motion valve, allows switching the fluid control valve into the second state. By means of the motion valve, in particular by means of the second switch state, the safety reached through the actuation unit is further increased. It may also be said that the second switch state enables an adjustment of a parameter that is to prevail or be observed for a switching of the fluid control valve, such as a pressure or a control signal, which may be present as a pressure level, for example. The fluid control valve requires a certain number of switching preconditions. One switching precondition, in order that the fluid control valve is capable of getting into e.g. the second state, may be set through falling below a threshold pressure. As a precondition in such a configuration, so that the fluid control valve actually reaches the second state, a pressure, in other words a pressure lower than a threshold pressure (i.e. a pressure at a low level) influences the switching in the first control line. Only by falling below said pressure, the fluid control valve can be switched from its first state in another state such as the second state. Exceeding the low pressure, i.e. a pressure beyond the low level, will block a motion of the fluid control valve, e.g. at least a piston into one motion direction.

The fluid control valve preferably has a pressure relief position. The pressure relief position may particularly be taken when the motion valve has the switch state of the first through- position. Preferably, a pressure relief position is present when the chamber assigned to the fluid control valve as a motion chamber of the actuator still prevails at a minimum size, a size due to performing as a clamping chamber. As a result, the pressure decrease in the motion chamber of the actuator can be initiated in an especially rapid manner. As one result, the holder can be opened without significant time delay. The term "motion chamber" refers to the chamber of the actuator that is connected to the fluid control valve. The motion chamber is preferably used for supplying a motion force to the clamping piston, in order to displace the clamping piston into a preferred position, particularly a closing position. Because of the usually very low material elasticity, the clamping chamber size has a greater volume than the motion chamber size in the closing position of the actuator. In the pressure relief position of the fluid control valve, a hold-open pressure acts on the fluid control valve via the first valve control line. Furthermore, the hold-open pressure prevails at the hold-open chamber. Preferably, the hold-open pressure is supplied by at least one motion valve in the first switch state. The first valve control line may be connected to the first control line via a two-position check valve.

A discharge opening is assigned to the valve control line, in other words connectable. A valve control line includes a discharge opening. The discharge opening may be closed to prevent fluid from flowing out of the discharge opening. In one switch state, the discharge opening facilitates the decrease of a pressure in the valve control line. By decreasing the pressure, the actuator is capable of taking a position in a more rapid manner. By opening the discharge opening, a relief path is released for the actuator, more precisely for a chamber of the actuator.

One approach to solving the present problem includes that the valve control of the fluid control valve is effected via an actuation pressure difference. It is possible to switch the bi-stable fluid control valve depending on an actuation pressure difference. An actuation pressure difference can for example be achieved in that a difference between a first actuation pressure and a second actuation pressure is detected or determined. In another configuration, an actuation pressure difference may be a difference between an actuation pressure and a threshold pressure. It is also possible to arrange a fluid control valve depending on two actuation pressure differences, such as a difference of a first actuation pressure of a first threshold pressure and a difference of a second actuation pressure of a second threshold pressure. A first actuation pressure is a fluid pressure prevailing at the actuation side of the fluid control valve. When the fluid pressure at the fluid limitation side is equal to or lower than a preset threshold pressure, a position change of the fluid control valve is allowed at this point. However, the fluid control valve may also depend on further actuation conditions. The position change of the fluid control valve advantageously results in that a clamping pressure is switched onto the actuator.

At the secondary control side, the fluid control valve may be supplied with a second fluid pressure. A fluid pressure prevailing as a second actuation pressure at the fluid control valve, allows switching the clamping pressure when the magnitude of the fluid pressure is greater than a second threshold pressure value. For example, a pressure value in the range of 1 bar, i.e. for example exactly 1 bar, may be preset at the fluid control valve as a second threshold pressure. A pressure value for the first threshold pressure and a pressure value for the second threshold value may be almost or actually identical, which is the case in many configurations of valves suitable as fluid control valves. It is advantageous to select valves having a most low hysteresis. In other embodiments, the hysteresis of the valve may be used intentionally. A second threshold pressure may be provided, which is e.g. 10% or 20% greater than the first threshold pressure, in order to facilitate the taking of a switch state (compared to other switch states).

The fluid control valve responds to the presence of fluid pressures at actuation points, e.g. at an actuation side or a secondary control side.

Switchable 3/2 valves (three/two valves) may be used as preferred valve types. 3/2 valves can be used for many valves. Due to their simple structure, the actuation unit may be designed in a particularly compact manner with 3/2 valves. Preferably, at least one valve is configured as 3/2 valve. The fluid control valve or at least one motion valve is suitable to that end, for example. It is also possible to configure at least one valve as an electromagnetically-switchable valve. As a result, actuation units can be integrated in electronic circuits of tooling machines or testing machines in an especially favorable manner. Another favorable configuration provides that at least one valve is mechanically-switchable. In a mechanically-switchable valve, e.g. electromagnetic interference can be prevented in high-sensitive material tests. Preferably, the fluid control valve is configured to be manually actuated at least at one side via a fluid pressure in order to be able to provide the intrinsic safety regardless of a current supply.

Advantageously, the fluid control valve is a pre-controlled valve. The fluid control valve may be arranged in a hydraulic line of an actuation unit. A pneumatic or hydraulic line may include the components pressure control valve, fluid control valve and port to the actuator. The particularly spring-loaded pressure control valve is connected to the fluid control valve at the entrance side. The pressure regulator (colloquial) or the pressure control valve is thus located at the entrance side of the fluid control valve when viewed pneumatically or hydraulically from the pressure source. The outlet of the fluid control valve is then connected to the actuator, more precisely to a clamping chamber of the actuator. By means of said switch configuration, a very specific, adjustable pressure may be provided to the actuator. The clamping chamber, i.e. the one that can be changed in size by means of the second actuator in case no force caused by pressure that is exceeding the force of the actuator is present in the opposing chamber, is provided or can be provided with an exactly defined pressure. Compared to the line leading to the clamping chamber, the pressure conditions in the remaining lines of the circuit may be uncontrolled. In the extreme case, it is readily sufficient when a minimum pressure is present, which results from the hysteresis of the fluid control valve, for example.

The minimum pressure of the circuit should prevail above a threshold, which depends on the hysteresis of the fluid control valve.

The fluid control valve is connected to a spring-loaded switch valve, preferably at the actuation side. Said spring-loaded switch valve may also be referred to a first spring-loaded switch valve.

Connection may be effected via a change valve. The fluid pressure is supplied to the fluid control valve via the first valve control line. The first valve control line can be formed as an actuation-sided connection of the fluid control valve to the change valve. In particular additionally, a second spring-loaded switch valve may be connected to the fluid control valve at the secondary control side. Preferably, a second valve control line connects a port, which is particularly intended for being connected to a secondary control line, of the fluid control valve to a second spring-loaded switch valve. Preferably, the switch valves are designed to function as two-position check valves. The two-position check valves may be functionally configured as free position valves, i.e. in the case of an insufficient supply of power or when not being actuated, the two-position check valve gets into a preferred position, in which the two-position check valve does not trigger a changed actuation of the fluid control valve. On one configuration, at least one of the first and second switch valve may have a first position. The first position is a preferred position due to the spring load. The preferred position particularly is a pressure relief position, in which one of the valve control lines has lost its pressure by way of the actuating medium flowing off. From one point of view, the pressure relief position may be referred to as fluid discharge position, because fluid is capable of flowing out of the respectively connected valve control line. Flowing-off is effected e.g. into a pressure-free reservoir. A second position of the at least first and second switch valve can e.g. be taken by means of a counter force against the spring load. The second position is a pressure-through-position. In other words, the pressure-through-position may be referred to as fluid pass-through position. The term "fluid pass-through position" means, according to one aspect, that fluid may flow into the valve control line. In the pressure pass-through position, the fluid is provided from a pressure source, which e.g. comprises a fluid pump or a fluid reservoir.

The circuit and actuation unit variants presented above result in a holder or a material testing machine, respectively, in which the closing speed of the clamping jaws of the holders is irrelevant as a result. Preferentially, the high level of safety is not searched for in a speed limitation during the closing motion of the clamping jaw, but by a limitation of other parameters such as at least one of a force and a pressure. The value known from standards and regulations of only 10 mm/sec or 600 mm/min for the movement velocity of the clamping jaw may be exceeded significantly. A material testing machine that is reliable and that involves only little accident risk at the same time due to the present (specimen) holder(s) is provided by the present invention, which may operate at any closing speed. That means that the closing or open position can and is allowed to be significantly quicker than 600 mm/min. A risk of fingers or hands being clamped between a specimen and a clamping jaw are no longer existent, but nevertheless the test-specimen to be tested (not yet applied with a testing force) can be clamped in an extremely short period of time.

The circuit presented can generally be used for any type of holder for material testing machine, regardless of the site of the clamping jaw. By means of the circuit, the force, alternatively the pressure, generated by the actuated clamping jaw can be restricted. Injuries of or on finger, skin, hands, feet, legs or trunk can be avoided, as long as values are below threshold values to be observed (e.g. less than 150 N, preferably less than 100 N or e.g. less than 2 to 3 N/mm$^2$.

However, from another or different point of view, one could also address the present invention as follows:

This invention starts with the conceptual idea that a complete de-coupling of the closing and opening at one side and of the clamping on the other side can be performed. The first clamping process or the release of a sample is effected as a closing or opening of a clamping jaw. Regardless thereof, provided that the closing position has been taken or prevails, the clamping process is performed with completely different, particularly higher, forces. A risk reduction is possible because opening and closing process are performed below at least one of a pressure and force threshold, which may be considered as unproblematic or not dangerous. Such forces may for example be set to 150 to 200 N or a pressure below 2 to 3 N/mm$^2$.

According to another aspect, the present invention makes use of the knowledge that it is not the closing velocity causing a hazard and accident injuries, but the forces and pressures occurring during the closing and clamping process. If a force limitation is effected during the closing process, the closing process can be considered uncritical.

Independent of the closing velocity, at least one of a force limitation and a pressure limitation of the actuator, the piston, the tappet or the clamping jaw is effected, in other words of a moving part, which may exert a force to a human body part.

According to a remarkable aspect, the pressure conditions in the actuator are evaluated. The prevalence of a clamping pressure, thanks to a controlling valve such as the fluid control valve, is only possible when the closing position has been taken and if the pressure in the hold-open chamber is below a minimum pressure, a threshold pressure. The pressures in the actuator are used for switching the controlling valve, i.e. particularly the fluid control valve. A hysteresis present in the controlling valve can be used for evaluation of the pressure in the actuator. A stabilized state results from to the hysteresis in the controlling valve, e.g. in the fluid control valve. The fluid control valve operates bi-stable in response to the pressure in the—connected —actuator(s).

It can also be emphasized that the actuator or the clamping jaw or the holder presents a special feature even to the reserved observer, who may only take note of the outer appearance. By default, the holder is in the closing position. According to one aspect, the closing position is the neutral position. The closing position is the preferred position. The closing position is considered a permanent position. Both clamping and open position can only be taken under the influence of pressures. If fluid pressure does not prevail at the actuator, e.g. pneumatic or hydraulic pressures, the actuator is in the closing position.

In particular a bi-directional, actuation motion unit may be provided in a material testing machine, which starting from a preferred direction is switchable for a movement into a second movement direction of the holder. A safety fluid pressure unit may operate, in particular bi- directionally, pressure-limited as a second and/or fourth actuator. In other words, the preferred position can be switchable e.g. from a first stop to a second, particularly opposite, stop. As a result, possible crushing injuries in any phase of the test-specimen exchange are almost excluded.

The above-described combinations and exemplary embodiments may also be contemplated in numerous other combinations.

SHORT FIGURE DESCRIPTION

The present invention can be better understood if reference is made to the attached figures, which figures present particularly advantageous exemplary embodiments by way of example, without limiting the present invention to these options, wherein:

FIG. 1 shows a first example of a hydraulic or pneumatic circuit for a material testing machine having a holder and an actuation unit, FIG. 2 shows a second example with reference to a circuit for a material testing machine having a holder and an actuation unit, FIG. 3 shows a further concept example of a material testing machine having a holder, wherein different variants for supplying a safety closing force are illustrated jointly, and FIG. 4 shows a very simplified illustration of the type of the load-frame testing machine, also referred to as column testing machine, as one embodiment of a particularly favorable material testing machine.

Figure 1:
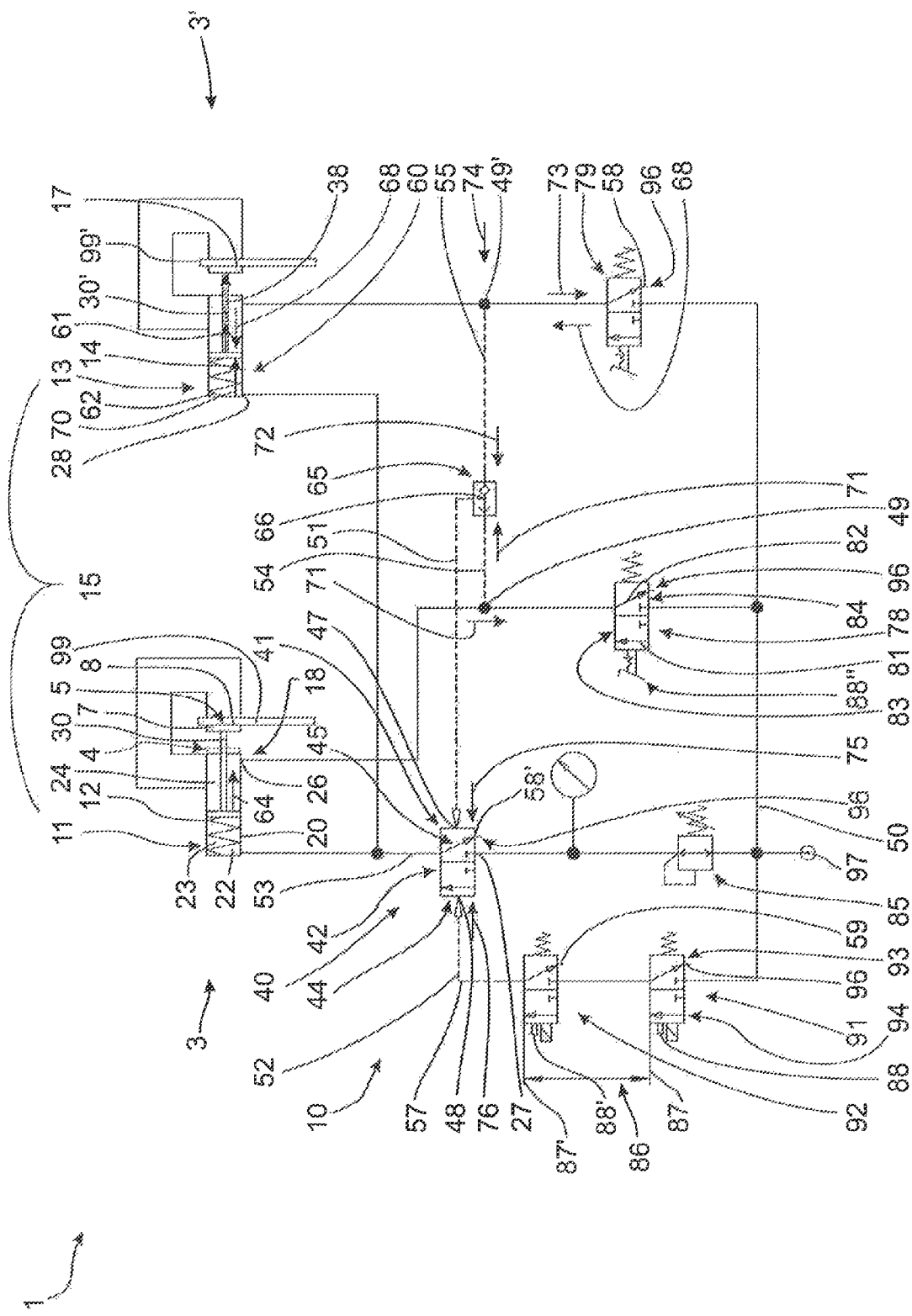
FIG. 1 shows the parts of a material testing machine 1 which essentially refer to a holder, namely the material testing machine 1 using the example of a first holder 3 and a second holder 3' as well as an actuation unit 10. Further components (not illustrated here) such as load-frames, driving traverse, control electrics, test software and load cells can, depending on which material tests, in particular in mechanic material loads, are to be performed—can be taken from the material testing concepts known from prior art. For reasons of clarity, reference is made to the section "Technical field", which could be included at this point in its entirety. In the first holder 3 is located the first actuator 11 in a closing position 5, which is why the clamping jaw 7 fits closely to the test-specimen 99. The closing position 5 of the actuator 11 ensures a like-wise prevailing closing position 8 of the clamping jaw 7. The actuator 11 allows that in the closing position 8 of the clamping jaw 7, inclinations on the test specimen 99 can easily (to a certain extend) be compensated. In the (dashed) illustration of the open position 4, the clamping jaw 7 touches at least one part of the housing of the linear cylinder 20, which is indicated schematically in FIG. 1 by means of the dashed line by a position indication for the clamping jaw 7. At least on portion of the clamping piston 30 is located in said linear cylinder 20. A subdivision of the linear cylinder 20 into a hold-open chamber 24 and a motion chamber 23 results from a penetration depth of the clamping piston 30. The motion chamber 23, shown in the closing position 5, may also be referred to as clamping chamber 22.

A second actuator 12 is arranged in the motion chamber 23. The actuator 12 is configured as a closing force limitation spring, of the same type as the spring 62. The safety closing force 61, which is performed by the spring 62, is thus limited in terms of its magnitude. A third actuator 13 is part of the second holder 3'. Together with the first actuator 11, the third actuator 13 forms a pair of actuators 15. A fourth actuator 14, in the form of the screw spring 62, performs tasks in the holder 3', just as the second actuator 12 in the holder 3. The fourth actuator 14 also provides an actuation force 64 in its functional equivalent to the second actuator 12, which actuation force presses the respective clamping pistons 30, 30' towards the material specimen supported on the holder 3, 3' in the closed actuation position, such as in the position 17. Said actuation force 64 on the clamping piston 30, 30' can just as well be understood as a closing pressure. The holders 3, 3' can also be referred to as clamping device 38 for the end positions of the specimens 99, 99'. The first actuator 11 and the third actuator 13 are hydraulically supplied with the pressure of a hydraulic medium (not indicated in the schematic plan) from the pressure source 97 via the line 50 for pressurized hydraulic medium.

A first pressure medium connection from the pressure source 97, controlled via the pressure control valve 85 to a pressure value adjustable from the outside to the motion chamber 23, can be achieved through the fluid control valve 40 by means of ports, such as port 28. The fluid control valve 40 comprises a first state 41 and a second state 42. The switch picture of FIG. 1 shows the fluid control valve 40 in the pressure-decrease position 45. Hydraulic mediums can flow-off in to the fluid reservoir 96 from the motion chamber 23.

In the case of existent switch conditions, the fluid control valve 40 can be switched in the first state 41 (the first state 41 may be abandoned), in order to take a pressure-built-up position 44. In the pressure-built up position 44, the pressure source 97 is through-connected to the motion chamber 23 by means of the fluid control valve 40. In the switched, first state 41 of the fluid control valve 40, the fluid control valve 40 of the first actuator 11, in particular of the clamping chamber 22, forms a discharge line 58'. The part of the connection 53, which is present between the fluid control valve 40 and the actuator 11 for guiding the fluid, serves as a fluid discharge line in the first switch state 41 and as a fluid supply line for the fluid to the clamping chamber 22 of the actuator 11 in the second switch state. Whether the preconditions for abandoning the second switch state 42 of the fluid control valve 40 into the first state are present or not results from the control pressures applied on the primary control side 47 and the secondary control side 48 of the fluid control valve 40, i.e. the first actuation pressure 75 on the primary control side 47 and the second actuation pressure 76 on the secondary control side 48 (the actuation pressures being symbolized by their equivalent forces). In the first state 41 of the fluid control valve 40, pressure-built-up is not possible in the clamping chamber 22.

The actuation force 64 contributes to discharging fluid from the hold-open chamber 24 via the fluid-flow-off-side 18, namely past the control branching 49 through the first motion valve 78 into the fluid reservoir 96. In this case, the first motion valve 78 is in a second switch state 84 and in this state comprises a second flow-through connection 82.

The motion valves, such as the first motion valve 78 and the second motion valve 79, have the same structure. The first motion valve 78 can be switched from the second switch state 84 to a first switch state 83. In the first switch state 83, the motion valve 78 establishes a first flow-through connection 81. A change of the state of the motion valves 78, 79 can be effected by means of a push-button, such as the push-button 88". In the first flow-through connection 81, the pressure source 97 is in fluid connection with the hold-open chamber 24 of the actuator 11.

In the second-flow-through position, indicated in FIG. 1 in the switched-on state, that means with the flow-through connection 82 of the motion valve 78 being provided, a fluid pressure prevailing in the hold-open chamber 24 gets to the change valve 65 as a first fluid flow-off pressure 71, which valve is a two-position check valve, when the fluid flows-off.

Figure 2:
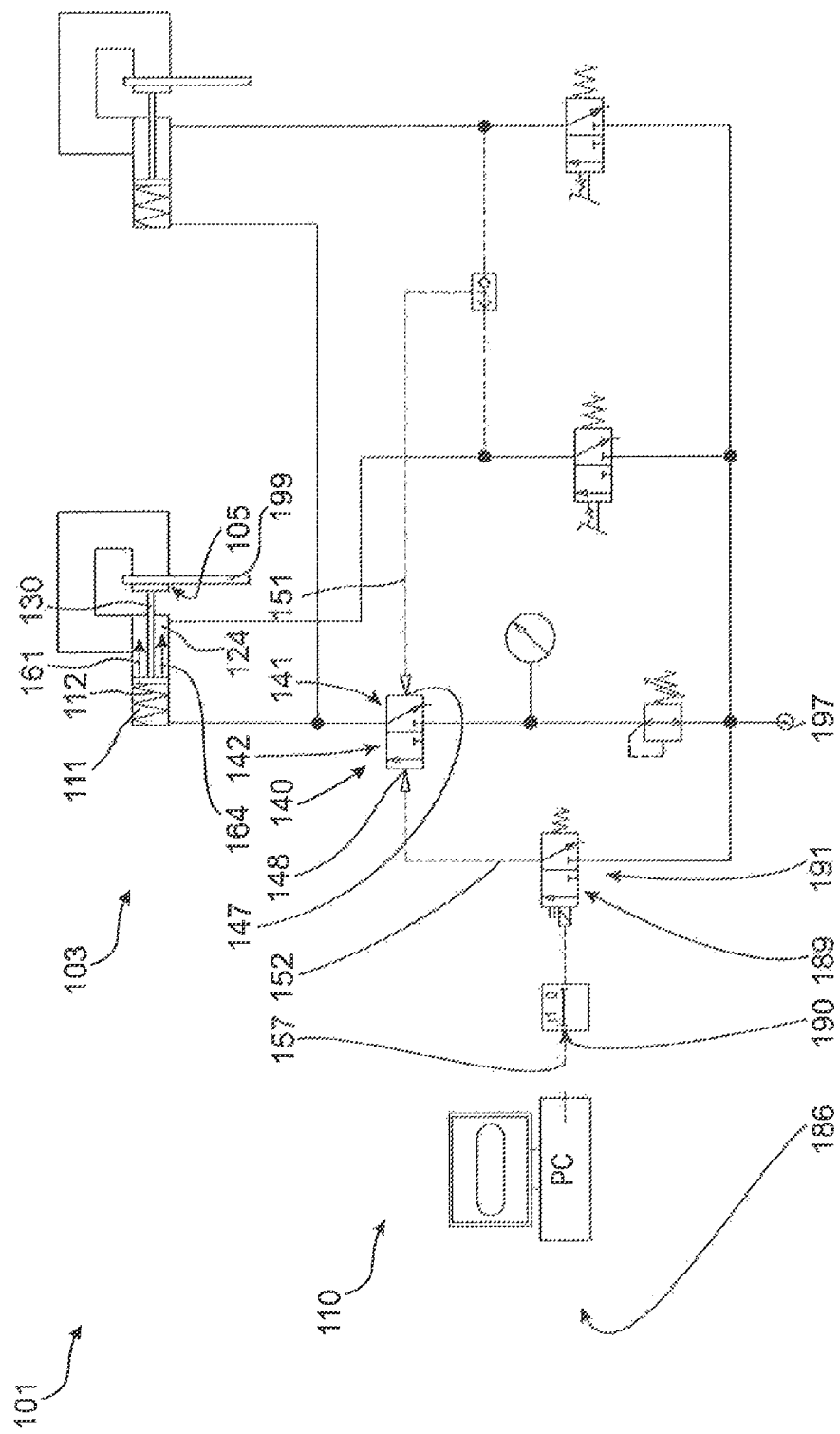
Figure 3:
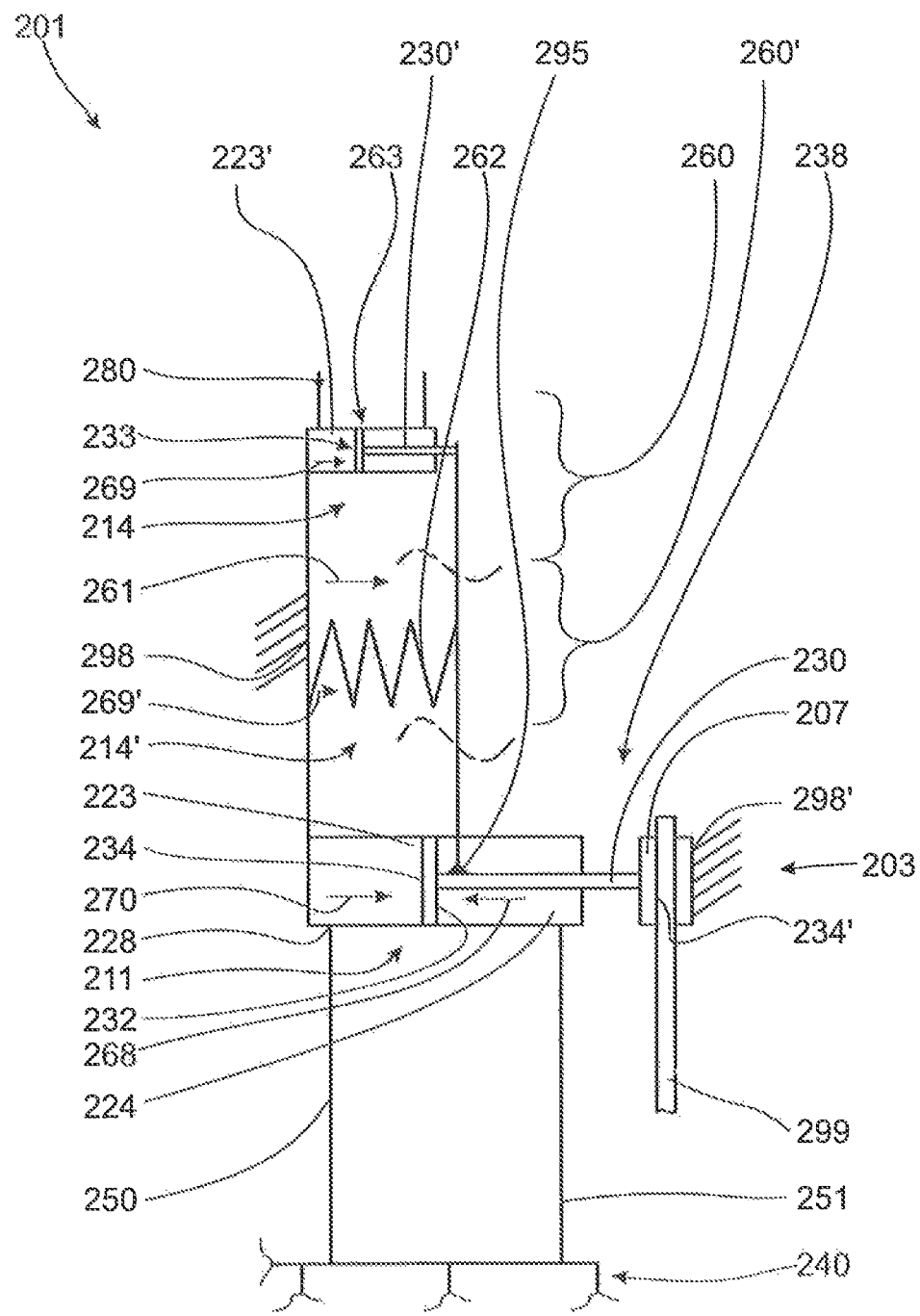

Here, it should be noted that the arrows indicated in FIG. 1 and the following FIGS. 2 and 3 schematically show a direction of the respective pressures, as for example of the fluid flow-off pressure 71, or a direction of these pressures.

The hold-open chamber 24, the first motion valve 78 and the double-position check valve 65 are interconnected hydraulically at the control branching 49. Via a first control line 54, fluid gets into the two-position check valve 65 from the control branching 49. In a corresponding manner, fluid from the third actuator 13 gets through the second motion valve 79 into the fluid reservoir 96. The line to the fluid reservoir 79 is a fluid flow-off line 58. Between the third actuator 13 and the second motion valve 79 is arranged a control branching 49', leading from the fluid pressure line through the second control line 55 to the second inlet of the double-position check valve 65, in particular connecting the third actuator 13 and the second motion valve 79 in a fluid manner. A second flow-off pressure 72 of the third actuator 13 prevails at the two-position check valve 65 through the control line 55. The pressure switch 66, realized by the two-position check valve 65, allows the higher one of the two flow-off pressures 71, 72 to flow into the first valve control line 51. In the position shown for the two-position check valve 65, the control pressure present in the form of the control pressure 75 is applied to the fluid control valve 40 from the hold-open chamber 24 via the valve control line port 26, via the control branching 49, via the two-position check valve 65 and the first valve control line 51 from the primary-control side.

If the first motion valve 78 is brought into the first switch state 83, the pressure from the pressure source 97 prevails through the control branching 49 and the two-position check valve 65 as a first actuation pressure 75 at the fluid control valve 40. However, in said switch state of the switch shown in FIG. 1, a pressure of the pressure source 97 located at the actuation side of the fluid control valve 40 is superior to a threshold value for the fluid control valve 40, which is therefore set to present first switched state 41, the pressure-relief position 45 for the motion chamber 23. The fluid flow-off pressures 71, 72 are maintained in particular by a displacement pressure 74 and a back pressure 73 upon flow-off of fluid from the actuators, such as the actuators 11, 13, until the back pressure 73 has completely decreased.

The input unit 86 is connected to the secondary control side 48 of the fluid control valve 40 via the second fluid control line 52. The port 27 at the fluid control valve 40, which is provided for a (indirect) connection of the pressure source 97, is closed in the first state 41 of the fluid control valve 40. If the actuators 11, 13 are located in a position such as position 17, in which position no (worth to mention) fluid can leak from the actuators 11, 13, the first control pressure 75 is below a threshold value. The fluid control valve 40 can be switched from the first state 41 into a second switch state 42. As long as the input unit 86 remains in a non-operational state, the fluid control valve 40 remains in the first state 41 in a stable manner. FIG. 1 shows the non-operational state, namely in that the first switch valve 91 and the second switch valve 92, which valves are fluidly, particularly hydraulically-connected in series, are located in a position, i.e. a fluid flow-off position 93. The fluid flow-off position 93 is a preferred position due to spring-loading in the switch valves 91, 92. The connection between the second valve control line 52 and the pressure source 97 can be interrupted by means of the switch valves 91, 92. The second valve control line 52 is connected to a flow-off opening 59 on the flow-in side by means of the second switch valve 92. The secondary control side 48 of the fluid control valve 40 is pressure-free. In the pressure-free state of the secondary control side 48, the fluid control valve 40 cannot be switched into the second state 42. The term pressure-free, depending on the specifically installed model of a fluid control valve 40, may in particular relate to an overpressure, which is 0 bar compared to a reference pressure, or to a second pressure dropped below a preset threshold value, but also to a differential pressure, to a pressure in a fluid accumulation container, which represents the reservoir 96. The pressure in the fluid accumulation container 96 can be in a range of ambient air pressure in terms of its magnitude.

For switching the second state 42, it is necessary to operate the push-buttons 88, 88', in each case provided in pairs, of the hold-to-run safety controls 87, 87'. The first switch valve 91 and the second switch valve 92 need to be displaced next to each other into a second position, such as the second position 94, in other words, must be in the second position at the same time. To that end, an operator has to use both of his or her hands, for example. By an actuation of the switching elements, i.e. switch valves 91, 92 in FIG. 1, a control command, e.g. in the form of a hydraulic pressure, is input to the fluid control valve 40 via line 57. The fluid pressure from the pressure source 97 is supplied to the secondary control side 48 of the fluid control valve 40 via the second valve control line 52. By means of this pressure, switching the fluid control valve 40 from the first state 41 into the second state 42 is effected. This enables a pressure transmission from the pressure source 97 into the clamping chamber 22 in the position, in which said process has been terminated, i.e. in the closed position 17 of the actuators 11, 13. An internal, control-pressure-sided pressure release of the fluid control valve 40 is yet another condition for the actual switching of the fluid control valve 40. The fluid control valve 40 operates due to the fulfilment of multiple switch conditions. Safe built-up of the clamping force via the clamping pressure 70 is effected, which pressure prevails in addition to the actuation pressure, respectively its equivalent, the actuation force 64. Test-specimens 99, 99' are safely held in the material testing machine 1.

After termination of the actuation of the switch valves 91, 92, the switch valves get back into the first position 93 by means of a spring force. When the bi-stable fluid control valve 40 is in the second state, the fluid control valve 40 also remains in the second state 42, i.e. in the pressure built-up position 44.

A change of state of the fluid control valve 40 from the second state 42 into the first state 41 can be achieved by actuating at least one of the motion valves 78, 79. By actuating the motion valves 78, 79, the motion valves 78, 79 are brought to the first switch state 83 from the second switch state 84, which had been taken due to spring-load, also considered the through-flow-position into the fluid reservoir 96. The motion valve 78 and the motion valve 79 can be actuated independently from one another, such that the motion of the first actuator 11 and the motion of the second actuator 13, in particular the opening, can be monitored independently from one another. By a certain non-simultaneity, safety is increased when removing the specimens. A synchronization of the actuation of the motion valves 78, 79 may constitute a time-save in one embodiment for an automated removal of specimens. Depending on whether the material testing machine 1 is designed for a manual insertion of specimens or an automated specimen feeder, control via the motion valves 78, 79 can be configured in a simultaneous or asynchronous manner. A hold-open pressure 68 is fed into the hold-open chamber, such as the hold-open chamber 24, which pressure takes effect at the control-side, i.e. at the primary control side 47, and displaces the fluid control valve 40 from a second switch state 42 into a first switch state 41. If only one of the motion valves 78, 79, is actuated, the respective actuator 13, 11 assigned to the non-actuated motion valve 79, 78 remains closed by the actuation force 64 of the actuation force limitation unit 60. This allows a safe removal of a test-specimen 99, 99' held on both sides.

FIG. 2 illustrates another material testing machine 101 by way of its schematically-illustrated hydraulic control, which control comprises numerous components and configurations according to the material testing machine 1 of FIG. 1. The explanations regarding FIG. 1 also apply to the embodiment according to FIG. 2 for the similarly or even identically realized assemblies or components; reference may therefore be made to FIG. 1 instead of a full explanation. As can be seen from FIG. 2, a fluid control valve 140 is arranged in the functional center of the schematic switch, which fluid control valve can take a first state 141 and a second state 142. The fluid control valve 140 is part of the control unit 110, via which the holder 103 is controlled, actuated and monitored. The safety closing force 161 is, for example, continuously provided as an actuation force 164 via an actuator, such as the first actuator 112. The second actuator 112 is arranged in the first actuator 11. The second actuator 112 displaces the clamping piston 130 into a closing position 105, in particular toward the test- specimen 199. In this motion phase, the phase of closing, fluid (not illustrated) is pressed out of the holding chamber 124 by means of the actuation force 164.

The actuation force 164 builds-up a displacement pressure, which displacement pressure is applied to the control side 147 of the fluid control valve 140 via the first fluid control line 151. The secondary control side 148 of the fluid control valve 140 is configured to be actuated via a second valve control line 152. The control unit 186 serves for actuating the switch valve 191. The control unit 186 comprises a control calculator computer of the material testing machine 101. The control calculator computer is capable of outputting an actuation control signal 190, which gets to the switch valve 191 via the switch signal line 157. The actuation control signal 190 is e.g. output after starting time 0 at an actuation time t1. The actuation control signal 190 controls the switch valve 191 that is configured to be actuated electromagnetically, in order that the switch valve 191 changes to the actuation state 189. The actuation state 189 corresponds to the second position 94 of the switch valve 91 in FIG. 1. The switch circuit according to FIG. 2 is therefore configured more simple in comparison to the switch circuit according to FIG. 1, such that the second switch valve 92 for the control unit 186 (shown in FIG. 2) is not provided or not required, respectively. The actuation state 189 is taken in a direction opposite the spring-load of the switch valve 191.In the spring-loaded preferred position of the switch valve 191, the pressure from the pressure source 197, as shown in FIG. 2, is blocked. In the actuation state 189, the pressure from the pressure source 197 is applied to the secondary control side 148 of the fluid control valve 140 via the switch valve 191 and through the second valve control line 152 in order to switch-through the fluid control valve 140 into the second state 142, depending on the pressure the control side. In order to provide a highest possible safety, the fluid control valve 140 can only be switched by control pressures via the valve control lines 151, 152. In the second state 142, pressure from the pressure source 197 is applied to the clamping piston 130, which pressure acts on the clamping piston 130 rectified to the actuation force 164. The clamping piston 130 touches the test-specimen 199 by its clamping force. In accordance with hydraulic practices, control lines, as control lines 151, 152 are illustrated in a dashed manner, in order to better distinguish them from pressure lines in the hydraulic switches. This enables a safe remote control of the material testing machine 101, in particular by a control computer PC.

FIG. 3 shows further advantageous examples of a material testing machine 201 by means of a sectional illustration of selected areas of the switch circuits according to FIG. 1 and FIG. 2. FIG. 3 illustrates areas around an actuator, such as the actuator 11, 111, or the actuator 13, 113 as an actuator 203 with some details, which can be realized alternatively or in addition to the exemplary embodiments shown in FIGS. 1 and 2. A holder 203 is illustrated schematically. The actuator 211 presses against the test-specimen 299 with the clamping jaw 207, wherein the clamping device 238 can reliably retain the test-specimen 299 by means of the actuator 211 and the support 298'. The clamping jaw 207 touches the test-specimen 299 with its clamping surface 234'. The hold-open chamber 224 of the actuator 211 is directly connected to the fluid control valve 240 (see the respective fluid control valves 40, 140 and their hydraulic supply from the pressure source 97, 197 in FIG. 1 or FIG. 2 as well as the secondary-sided ports) via the first valve control line 251. The pressure (fluid) line 250, starting at the fluid control valve 240, is connected to the motion chamber 223 of the actuator 211 via port 228. Depending on the state of the fluid control valve 240, a clamping pressure 270 can be applied to the clamping face 234 via the port 228. The movable hold-open surface 232 limits the hold-open chamber 224. In order to open the actuator 211, the hold-open surface 232 can be applied with fluid pressure via the first valve control line 251 by means of another switch valve (not shown, see switch valve 78 of FIG. 1). If a fluid flows into the hold-open chamber 224 along with its pressure, a hold-open pressure 268 moves the clamping piston 230 with the clamping jaw 207 away from the test-specimen 299. The preferred position of the clamping piston 230 with the clamping jaw 207 on the test-specimen 299 is taken by means of one of the exemplary shown actuation-force limitation units 260, 260', which in particular provide the actuation force 261, if at least one actuation-force limitation unit 260, 260' corresponding to the examples is provided.

It should eventually be mentioned that the length of the pressure arrows or force arrows merely indicates a magnitude, but shall not to be understood as an exact representation of a relationship between the present pressures or forces. The exact configuration of said relationship is determined by any respective application.

A second actuator 214 is provided in the fore limitation unit 260, which actuator is supplied by means of a fluid pressure limiter 280. The fluid pressure acts on the drive surface 233 and generates a closing pressure 269 in the motion chamber 223'. Supported against a joint support 298, provided as support for the actuator 211 and the actuator 214, the piston 230' pushes the piston 230 in direction of a test-specimen 299 via a mechanical connection. Besides the second actuator 214', performing in the sense of a hydraulic rotor, another actuator 214' performing in the sense of a spring actuator can be provided.

It is also possible to provide the differently-structured second actuator 214' as an alternative to the second actuator 214. As mentioned, it is possible to combine a second actuator 214 with a second actuator 214' in one embodiment, in order to provide an actuation force limitation unit 260, 260'. The actuation force limitation unit 260' includes a spring 262 as a second actuator 214', the force of that spring 262 is limiting the safety power vector 261. In one embodiment, the spring 262 may provide a closing pressure 269'. The closing pressure 269' moves the clamping piston 230 toward the direction of the hold-open pressure 268 via the mechanical connection, until the clamping surface 234' touches the material specimen 299.

The fluid pressure cylinder unit 263 as well as the spring 262 can be arranged outside the second actuator 211 in this case. This facilitates the control of the reliable function of the actuating force limitation units 260, 261.

FIG. 3 schematically shows the components of the actuating force limitation units 260, 260' with a lateral displacement relative to the clamping piston 230, by means of which the schematic illustration of the embodiments can be seen particularly well. Such an arrangement, primarily illustrated schematically in FIG. 3, can also favorably be arranged offset in a three- dimensional design due to the available construction space - in accordance with the illustration. In order to reduce friction and to avoid transverse forces, for example, an actuation limitation unit 260, 260' is preferably arranged toward an actuator 211, wherein the safety force vector 261 is preferably arranged directing to an actuator 211, wherein the safety force vector 261 is directed to an axis with the clamping pressure 270 along the clamping piston 230. According to another aspect, the safety force vector 261 is preferably introduced by a second actuator 214, 214' arranged on a central axis (not illustrated) along the clamping piston 230.

Figure 4:
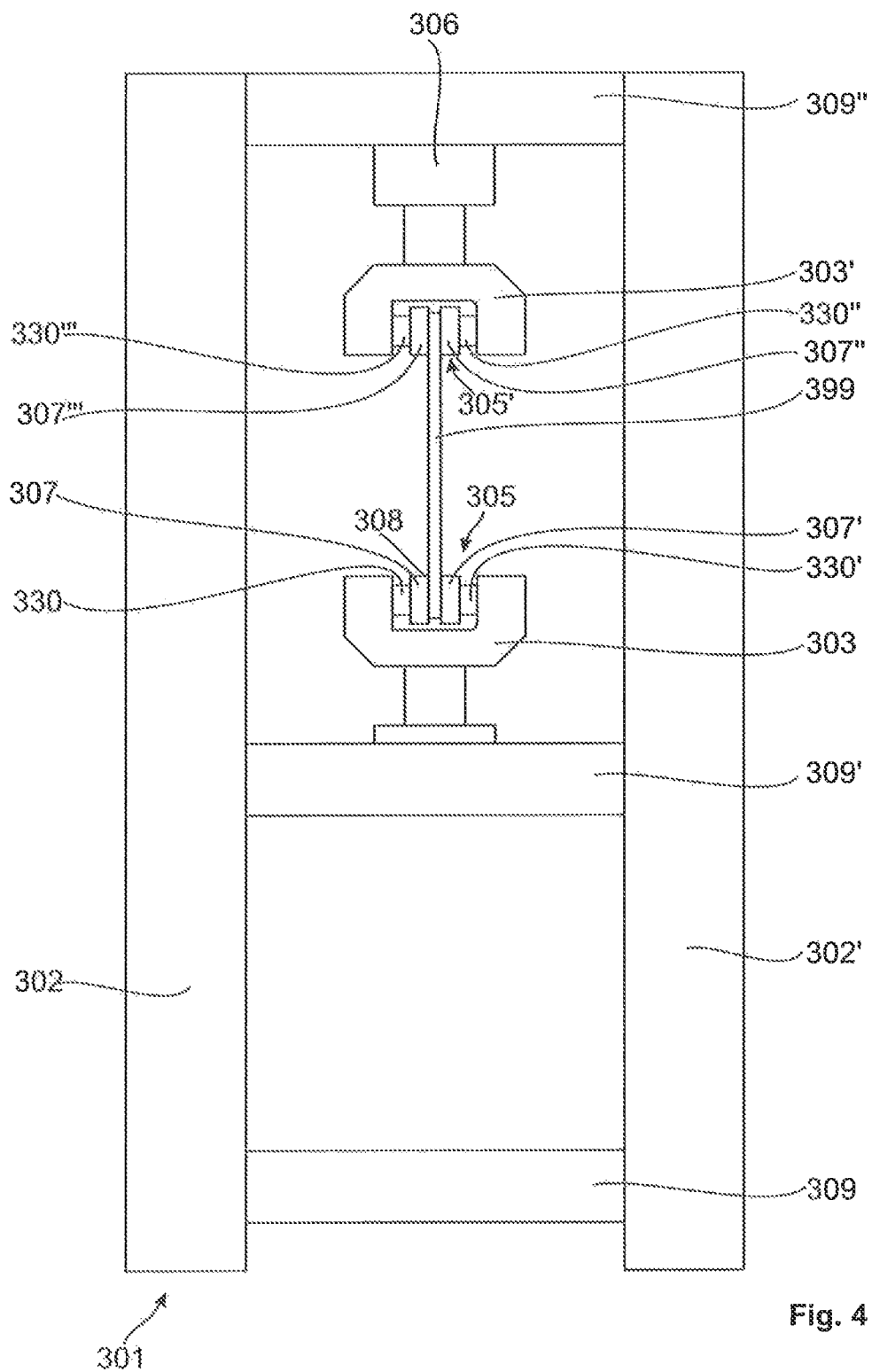

FIG. 4 shows, in a simplified illustration, the type of a column testing machine as a material testing machine 301. The column testing machine, which is occasionally also referred to as traverse testing machine, comprises at least two columns, a first column 302 and a second column 302'. Traverses 309, 309', 309" are attached to the two columns 302, 302' running transversely to the extension direction of the columns 302, 302'. The two outer traverses 309, 309" are provided as base traverses 309 and as a head traverse 309"'. Between the base traverse 309 and the head traverse 309"' there is a travel traverse 309'. The travel traverse 309' is located in the middle region on the two columns 302, 302'. A force can be applied to a test-specimen 399 by means of the travel traverse 309'. The two outer traverses, the base traverse 309, and the head traverse 309", form a frame together with the two columns 302, 302'. A testing space is located between the columns 302, 302', in which space can be arranged the test-specimen 399. In order that a testing force can be applied to the specimen 399, the specimen is clamped between the clamping jaws 307, 307', 307", 307'''. The clamping jaws 307, 307', 307", 307''' are guided and moved by clamping pistons 330, 330', 330", 330". One clamping piston 330, 330' 330", 330''' is assigned to each of the clamping jaws 307, 307', 307" 307'''. By means of the clamping pistons 330, 330', 330", 330''', the holders 303, 303' can be brought in to a closing position 305, 305'. In the closing position 305, 305' the portion of the specimen touching the clamping jaws 307, 307', 307", 307''' is held in a force-fit manner. The closing position 308 of the clamping jaws 307, 307' corresponds to the closing position 305 of the holder 303. If the clamping jaws 307, 307' are in a closing position 308, the holder 303 surrounding the clamping jaws 307, 307' is also in a closing position 308. If the force in the closing position 308 of the clamping jaws 307, 307" is sufficiently great, a testing force can be applied to the test-specimen 399 by means of a displacement of the travel traverse 309'. The testing force or respectively the forces acting in the material testing machine 301, which in particular act on the specimen 399, can be measured by means of a force transducer 306. A favorable place for detecting the measurement force by means of a force transducer is a bottom side of the head traverse, preferably in the immediate axial extension of a clamping direction of the test-specimen 399. The second holder 303' is used as a counter- holder. The first holder 303 serves a force-exerting holder. The force transducer 306 rests against the head traverse 309"'. For closing the clamping jaws 307, 307', 307", 307''' the material testing machine 301 can be equipped with an actuation unit, such as e.g. the actuation unit 10 (FIG. 1) or the actuation unit 110 (FIG. 2).

At this point it might be worth pointing out the achievement that the respective actuation force limitation units 260, 260' can be upgraded or replaced on the material testing machines 1, 101, 201 involving little effort only. The actuation force limitation units 260, 260' can be designed as an upgrade kit. The actuation force limitation units 260, 260' can also be used for moving a holder of a protection device, such as a protection case, in order to thus protect access to e.g. a material testing machine operating with particularly high forces.

The configuration options shown in the individual figures FIG. 1, FIG. 2, FIG. 3 and FIG. 4 can be combined with one another in any desired manner. In particular, elements of one embodiment can advantageously be combined with another embodiment.

It shall be understood by a person of ordinary skill in the art that the application of the invention described by means of FIG. 4 can just as well be transferred to a column testing machine, forming a frame for a test space by means of a higher or lower number of columns. The invention can just as well be used in C-shaped testing machines, so-called single-column machines,—and also be upgraded, as in material testing machined having three, four or more columns.

Reference Numeral List

| Reference Numeral | Name |
| --- | --- |
| 1, 101, 201, 301 | Material testing machine |
| 302, 302' | Column, in particular first column and second column |
| 3, 3', 103, 203, 303, 303' | Holder |
| 4 | Open position, in particular of the holder |
| 5, 105, 305, 305' | Closed position, in particular closed holder |
| 306 | Force transducer |
| 7, 207, 307, 307', 307", 307'" | Clamping jaw, in particular holding jaw |
| 8, 308 | Closed position of clamping jaw |
| 309, 309', 309" | Traverse, in particular base traverse, travel traverse and head traverse |
| 10, 110 | Actuation unit |
| 11, 111, 211 | First actuator |
| 12, 112 | Second actuator |
| 13 | Third actuator |
| 14, 214, 214' | Fourth actuator |
| 15 | Actuator pair |
| 17 | Actuator position, in particular closed position |
| 18 | Fluid discharge side, in particular of an actuator |
| 20 | Linear cylinder |
| 22 | Chamber of the actuator, in particular clamping chamber |
| 23, 223, 223' | Chamber of the actuator, in particular motion chamber |
| 24, 124, 224 | Chamber of the actuator, in particular hold-open chamber |
| 26 | Valve control line port |
| 27 | Connection for pressure source |
| 28, 228 | Connection to actuator |
| 30, 30', 130, 230, 230', 330, 330', 330", 330'" | Clamping piston |
| 232 | Hold-open face |
| 233 | Actuation face |
| 234, 234' | Clamping face |
| 38, 238 | Clamping device |
| 40, 140, 240 | Fluid control valve |
| 41, 141 | First state, in particular of fluid control valve |
| 42, 142 | Second state, in particular of fluid control valve |
| 44 | Pressure built-up position of fluid control valve |
| 45 | Pressure built-down position of fluid control valve |
| 47, 147 | Primary control side of fluid control valve, in particular actuation side |
| 48, 148 | Secondary control side |
| 49, 49' | Control branching |
| 50, 250 | Line for pressurized medium |
| 51, 151, 251 | First valve control line |
| 52, 152 | Second valve control line |
| 53 | Connection line |
| 54 | First control line |
| 55 | Second control line |
| 57, 157 | Line, in particular for a switch signal |
| 58, 58' | Fluid discharge line |
| 59 | Discharge opening |
| 60, 260, 260' | Actuation force limitation unit |
| 61, 161, 261, | Safety closing force, in particular safety force vector |
| 62, 262 | Spring, in particular limited closing-force spring |
| 263 | Fluid pressure cylinder unit, in particular closing-force limitation |
| 64, 164 | Actuation force |
| 65 | Change valve, in particular two-position check valve |
| 66 | Pressure switch, in particular passage for highest pressure |
| 68, 268 | Hold-open pressure |
| 269, 269' | Closing pressure |
| 70, 270 | Clamping pressure |
| 71 | First fluid flow-off pressure |
| 72 | Second fluid flow-off pressure |
| 73 | Back pressure |
| 74 | Displacement pressure |
| 75 | First control pressure |
| 76 | Second control pressure |
| 78 | First motion valve |
| 79 | Second motion valve |
| 280 | Pressure limiter |
| 81 | First flow-through position, in particular flow-through connection |
| 82 | Second flow-through position, in particular flow-through connection |
| 83 | First switch state of motion valve |
| 84 | Second switch state of motion valve |
| 85 | Pressure control valve |
| 86, 186 | Input unit |
| 87, 87' | Hold-to-run safety control |
| 88, 88', 88" | Push-button |
| 189 | Actuation state |
| 190 | Actuation control signal |
| 91, 191 | First switch valve, in particular pressure spring-loaded switch valve |
| 92 | Second witch valve, in particular pressure spring-loaded switch valve |
| 93 | First position of switch valve, in particular, fluid discharge position |
| 94 | Second position of switch valve, in particular fluid intake position |
| 295 | Mechanical connection |
| 96 | Fluid reservoir, in particular sump |
| 97, 197 | Pressure source |
| 298, 298' | Support |
| 99, 99', 199, 299, 399 | Test-specimen, in particular end portion for clamping |
| PC | Control computer, in particular start of tests |
| t1 | Actuation time |
| 0 | Start time |

What is claimed is:

1. A holder having an actuation unit comprising:
at least a first actuator that can be loaded by a fluid from a pressure source, wherein a bi-stable fluid control valve is provided between the pressure source and the first actuator, the fluid control valve comprising at least a first and a second state,
and wherein the first actuator includes at least one clamping piston, wherein through the first actuator, by means of the clamping piston and an actuation force from a second actuator, which is connected to the clamping piston, a closing position can be taken,
and in that the fluid control valve changes into the second state only when a pressure, which originates from a chamber of the first actuator, reaches below a threshold pressure in a first valve control line, and when a change signal prevails at the fluid control valve in a second valve control line.

2. The holder according to claim 1, wherein the second actuator comprises an actuating force limitation unit, which provides the actuating force.

3. The holder according to claim 1, wherein the first actuator includes a linear cylinder that can be loaded by a source pressure, which comprises an end-sided valve control line port.

4. The holder of claim 3, wherein
the linear cylinder comprises a hold-open chamber and a fluid flow-off pressure of the hold-open chamber prevails through the valve control line at the fluid control valve at the actuation side and opposes a pressure build-up position of the fluid control valve being connected to a pressure regulation valve at the input side.

5. The holder according to claim 1, wherein
at least two actuators, the first and a third actuator, are provided and at least one change valve is arranged downstream the first and the third actuators at a fluid flow-off side, and a greatest fluid flow-off pressure of the actuators prevails at the fluid control valve as actuating pressure by means of the change valve.

6. The holder according to claim 1, wherein
the clamping piston comprises a pressure-loadable hold-open face, wherein, in an open position of the clamping piston, a pressure-loadable actuation face of the clamping piston is fluid pressure-relieved by a fluid discharge line.

7. The holder according to claim 1, wherein
a limited closing-force spring and/or a closing-force-limitation fluid pressure cylinder unit is assigned to the clamping piston at least at one side, by means of which the clamping piston is displaceable.

8. The holder according to claim 1, wherein
the actuation unit includes an input unit which is a hold-to-run safety control, and
a position change of the fluid control valve can be initiated by the input unit.

9. The holder according to claim 1, wherein
the actuation unit includes at least one motion valve comprising at least a first and a second flow-through position, wherein
in the first flow-through position, fluid gets into a first control line for building up a pressure with pressure provided from the pressure source, and, in the second flow-through position fluid from the first control line, with fluid flow-off from the first control line being opposed by a back pressure or a displacement pressure, gets into a fluid reservoir.

10. The holder according to claim 9, wherein
at least one of the motion valves has at least one switch state, wherein in one switch state, a pressure and/or control signal adjustment is enabled in a line by means of which a switch condition for the fluid control valve to get into its second state is given.

11. The holder according to claim 1, wherein
the fluid control valve has a pressure decrease position, wherein the pressure decrease position can be taken if a motion chamber of the actuator prevails in a clamping chamber size and a hold-open pressure is switched through to the first valve control line.

12. The holder according to claim 1, wherein
a closable discharge opening is assigned to the first valve control line.

13. The holder according to claim 1, wherein
the fluid control valve is configured as a 3/2-valve.

14. The holder according to claim 1, wherein
the fluid control valve is a pilot-controlled valve.

15. The holder according to claim 1, wherein
at least one first spring-loaded switch valve is connected to the fluid control valve at an actuation side, wherein
a first position of the first and/or a second switch valve is a pressure relief position with respect to one of the valve control lines, and a second position of the first and/or second switch valve is a pressure-through position, with respect to the valve control lines.

16. The holder of claim 1, wherein
the holder is a holder of a material testing machine for test-specimens, wherein the closing position can be taken by at least one clamping jaw of the holder.

17. The holder of claim 1, wherein
at least one actuation pressure difference at the fluid control valve allows switching a clamping pressure of the fluid control valve, wherein a fluid pressure at an actuation side is equal to or less than the threshold pressure in the first valve control line and a fluid pressure at a secondary control side is greater than a second threshold pressure, and a change valve is a two-position check valve switchable by pressure differences, which allows an higher pressure of two flow-off pressures to flow into the first valve control line.

18. A system for actuating at least one holder having an actuation unit, comprising:
at least one connecting line for pressurized medium, at least one actuator, and at least one bi-stable fluid control valve, and
the fluid control valve is connectable to a pressure source of a fluid and a closing position can be taken by the actuator,
wherein in the actuator, a safety closing force counteracts a hold-open pressure,
wherein the hold-open pressure sets a hold-open state of the fluid control valve, and wherein a build-up of a clamping pressure, which counteracts a direction of the hold-open pressure in the actuator, is provided in the actuator from the pressure source through the fluid control valve after a decrease of the hold-open pressure in the closing position of the actuator, wherein the actuation unit includes an input unit which is a hold-to-run safety control inducing a through state of the fluid control valve.

* * * * *